United States Patent
Grenon

(10) Patent No.: US 6,258,033 B1
(45) Date of Patent: Jul. 10, 2001

(54) ULTRASOUND METHOD EMPLOYING ECHOES FROM A REGION OF INTEREST TO ENABLE QUANTIZATION OF BACKSCATTER SIGNALS

(75) Inventor: Stephen M Grenon, Hillsborough, NC (US)

(73) Assignee: Agilent Technologies, Inc., Palo Alto, CA (US)

(*) Notice: Subject to any disclaimer, the term of this patent is extended or adjusted under 35 U.S.C. 154(b) by 0 days.

(21) Appl. No.: 09/451,298

(22) Filed: Nov. 30, 1999

(51) Int. Cl.[7] ........................................... A61B 8/00
(52) U.S. Cl. ................................................. 600/458
(58) Field of Search ................... 600/443, 444, 600/447, 458, 459

(56) References Cited

U.S. PATENT DOCUMENTS

| | | |
|---|---|---|
| 4,873,984 | 10/1989 | Hunt et al. . |
| 5,063,931 | 11/1991 | Leavitt . |
| 5,235,984 | 8/1993 | D'Sa . |
| 5,469,849 * | 11/1995 | Sasaki et al. ........................ 600/458 |
| 5,538,003 | 7/1996 | Gadonniex et al. . |
| 5,577,505 | 11/1996 | Brock-Fisher et al. . |
| 5,735,281 | 4/1998 | Rafter et al. . |
| 5,749,364 * | 5/1998 | Sliwa, Jr. et al. ..................... 600/458 |
| 5,873,829 * | 2/1999 | Kamiyama et al. ................... 600/443 |
| 6,146,330 * | 11/2000 | Tujino et al. ........................ 600/443 |

* cited by examiner

Primary Examiner—Peter Vo
Assistant Examiner—Maulin Patel

(57) ABSTRACT

The method of the invention controls an ultrasound unit to characterize echo signals from a region of interest (ROI) and to adjust unit parameters in accord therewith. The method initially defines a region of interest within an ultrasound image and processes received echo values from the region of interest to determine characteristics of the received echo values. Then at least one system parameter of the ultrasound unit is adjusted to cause the received echo values from the ROI to exhibit a desired characteristic. The derived system parameter is then used to control the ultrasound unit to produce a subsequent ultrasound image that includes the ROI as a portion thereof. The method of the invention further enables a user of an ultrasound system to obtain a quantitative measure of blood perfusion of an investigational region of interest (IROI), Data from a normalization region of interest (NROI) is used to create a normalization value to characterize the image echoes from the NROI. Thereafter, the normalized values of the image backscatter values are calculated through use of the normalization value and an image of the IROI is displayed, using the image echo values from the IROI.

22 Claims, 4 Drawing Sheets

ULTRASOUND METHOD EMPLOYING ECHOES FROM A REGION OF INTEREST TO ENABLE QUANTIZATION OF BACKSCATTER SIGNALS

FIELD OF THE INVENTION

This invention relates generally to ultrasonic imaging and, more particularly, to a method for providing an ultrasound system with an ability to quantitatively assess tissue perfusion, when contrast agents are in use.

BACKGROUND OF THE INVENTION

The use of ultrasound contrast agents has become more popular in recent years. Many manufacturers currently have a variety of agents under development. Each ultrasound contrast agent responds differently when exposed to ultrasound energy, which can pose a problem if the ultrasound system is not aware of the agent being utilized. In addition, the concentration of the agent and its injection rate also affects the quality of the derived ultrasound image. For example, too much contrast agent will prevent the ultrasound energy from penetrating into the body, while too little agent will not be visible in the resulting image. In addition, if the rate of the contrast injection varies significantly as the ultrasound images are acquired then it is difficult to determine if the changes seen in the images are caused by actual disease or just fluctuations in injection rates. In summary, there exist three problems, which the invention described below addresses.

1. Different ultrasound responses caused by different contrast agents may cause certain features of an ultrasound machine to work incorrectly or not work at all.

2. The amount of contrast agent injected can affect the image in a detrimental way. Too much agent will not allow the ultrasound energy to penetrate into the body and too little agent will not be detectable by diagnostic ultrasound.

3. A varying injection rate of contrast agent (e.g. bolus injections) will affect the user's ability to quantify changes in the ultrasound images over time. For example, if more contrast is injected at time T1 and less contrast agent is injected at time T2, current state of the art ultrasound machines have no way of determining if the change is due to a body's anatomical function (e.g., a lack of blood flow at T2) or if the cause is a lower amount of agent.

Contrast agents are used in assessing myocardial perfusion and comprise microbubbles that are approximately the size of red blood cells or smaller and are released as a bolus or by continuous infusion into the blood stream. During subsequent imaging, the region of the myocardium with the greatest microbubble concentration appears as a region of higher intensity backscatter in the ultrasound image. This intensity decreases at a rate dependent upon the rate of perfusion through the myocardial tissue.

The relationship between the microbubble concentration and the gray level intensity of the ultrasonic image is nonlinear. The non-linearity of signal return is due, in part, to the transmit voltage level. The level of the transmit voltage, its frequency, cycle count and pulse repetition rate lead to a "contrast stability model" (hereafter referred to as "CSM"). Each CSM defines how the microbubbles react in the presence of the ultrasound signals—which reaction is a direct function of the transmit voltage. There are three known modes of CSM operation. Linear CSM is that region of transmit voltages where the contrast agent is virtually undamaged by the incident acoustic signals and occurs at low transmission voltages. The nonlinear CSM mode is that region of transmit voltages which do not instantly destroy the contrast agents, yet produce sufficiently strong acoustic signals to cause the backscatter to exhibit harmonic energies that are detectable by the ultrasound transducer. This mode occurs at medium to high transmission voltages. Lastly, the destructive CSM mode occurs at high levels of transmit power and is the region where the microbubbles are destroyed, either totally or in part.

Clearly, the relationship between the CSM mode and the transmit sequence is dependent on the type and amount of contrast agent used, variability's between patients and in the same patient, over time. Each of these variables contribute to variations in the sensed level of echo signals which make accurate quantification of the perfusion level difficult.

The prior art describes a number of methods for approaching the backscatter quantification problem. U.S. Pat. No. 5,235,984 to D'Sa, (assigned to the common assignee as this Application) describes an ultrasonic imaging system wherein selected pixel values are processed to compute an average acoustic intensity thereof. The average value is then processed to reverse any nonlinearities between the calculated average value and the originally received acoustic signals, which non-linearities may have been introduced by the processing. The processed average acoustic intensity is plotted and the procedure repeated at specified time intervals to form a time-intensity curve whose characteristics are linearly related to the originally received acoustic signals.

U.S. Pat. No. 5,063,931 to Leavitt (assigned to the same assignee as this Application) describes a method for providing gain control in a Doppler ultrasound system. The Leavitt patent teaches the generation of a training line of acoustic backscatter signals through the region of interest being imaged. Information from the backscatter that results from the training line is then utilized to maximize the gain when the scan lines are in a flow medium, while being controlled so as not to saturate the system in general. Accordingly, the same backscatter that is received from a training line within the region of interest is utilized to calibrate the return from that region of interest.

U.S. Pat. No. 5,577,505 to Brock-Fisher et al. (assigned to the same assignee as this Application) describes an ultrasound system which measures the system response under multiple excitation levels. The responses gathered from the multiple excitation levels are gain-corrected in an amount corresponding to the difference in excitation levels, and are then subtracted. Because of this subtraction, most of the linear response is removed and what remains corresponds to the nonlinear response.

U.S. Pat. No. 5,735,281 to Rafter et al. (assigned to the same assignee as this Application) is directed at resolving some of the problems created by the destruction of contrast agent microbubbles. The duration and intensity of a contrast effect is greatly diminished by conventional imaging frame rates and power levels. Altering the imaging sequence by shooting ultrasound image frames at various transmit powers and reducing the number of transmit lines per frame, allows for enhancement of the contrast effect. In effect, the Rafter et al. system enables alteration of the transmission signals to achieve the enhancement of return from a region of interest.

Additional references which speak to applications of gain control and gain assessment can be found in the following patents: U.S. Pat. No. 5,538,003 to Gadonniex et al. and U.S. Pat. No. 4,873,984 to Hunt et al., both assigned to the same assignee as this Application.

Notwithstanding the teachings of the above referenced prior art, there still remains a need for a relatively simple, real time method for enabling a quantitative assessment of tissue perfusion, when using contrast media. In addition, there is a need for a real time method of controlling the response of the contrast media to the incident ultrasound signals. Further, the method should take into account and accommodate different types of contrast agents, and variability's between patients and in a same patient, over time.

SUMMARY OF THE INVENTION

The method of the invention controls an ultrasound unit to characterize echo signals from a region of interest (ROI) and to adjust unit parameters in accord therewith. The method initially defines a region of interest within an ultrasound image and processes received echo values from the region of interest to determine characteristics of the received echo values. Then at least one system parameter of the ultrasound unit is adjusted to cause the received echo values from the ROI to exhibit a desired characteristic. The derived system parameter is then used to control the ultrasound unit to produce a subsequent ultrasound image that includes the ROI as a portion thereof.

The method of the invention further enables a user of an ultrasound system to obtain a quantitative measure of blood perfusion of an investigational region of interest (IROI). Initially, a normalization region of interest (NROI) is ultrasonically examined. In a preferred embodiment, the NROI is positioned so as to be a source of blood for the IROI. The ultrasound system then determines a normalization value of the image backscatter values from the NROI. Thereafter, image backscatter values are acquired from the IROI, and normalized values of the image backscatter values are calculated through use of the normalization value and may be displayed. Thereafter, the ultrasound image of the IROI is displayed, using the image backscatter values from the IROI which have been normalized to the NROI.

More specifically, the user of the ultrasound device selects a region of interest on the displayed image with a pointing device, such as a trackball. This region of interest is selected in such a manner as to indicate to the ultrasound unit where the contrast agent is expected to be present in vivo. Once the region of interest is selected, the ultrasound machine is operated to transmit and process the return echo in that region to fully characterize the contrast agent's interaction with the ultrasound energy. This may eliminate a need to specify the actual agent being utilized. Further, by characterizing the agent in vivo, the ultrasound unit is able to determine if the contrast agent is capable of performing the operation specified by the user.

One of the characteristics which can be determined using this invention is whether or not the agent can be destroyed and if so at what ultrasound exposure level does it occur. This provides the user with the ability to determine how effective the agent will be for the particular diagnostic modality.

DETAILED DESCRIPTION OF THE INVENTION

Figure 1:
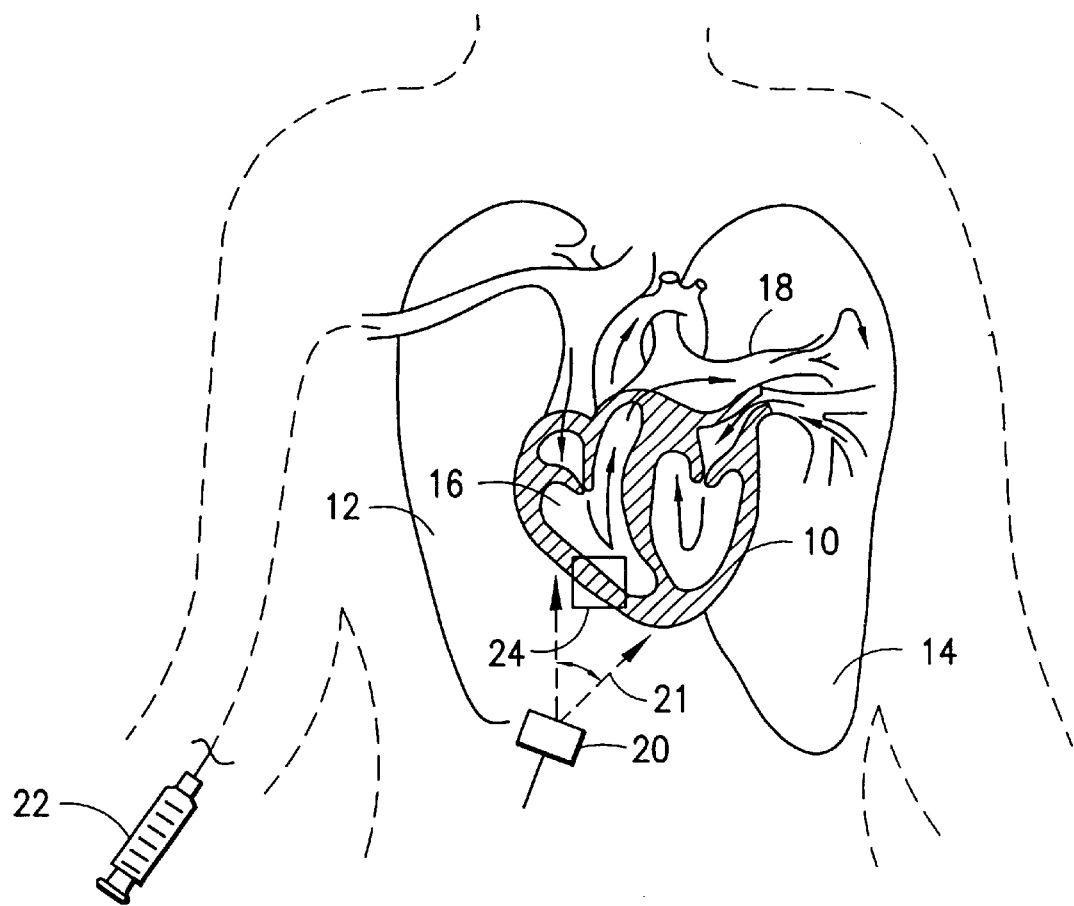
FIG. 1 illustrates an exemplary anatomical region and placement of an ultrasound transducer with respect thereto.

Referring to FIG. 1, the anatomy shown therein illustrates the relative positioning of heart 10, and lungs 12 and 14. Left ventricle 16 of heart 10 provides the blood pool 17 from which blood flows to left ventricular tissue 16 via coronary arteries (not shown) and pulmonary artery 18. It is to be hereafter understood, that it is desired (as an example) to image the blood pool 17, using ultrasound transducer 20 and acoustic beam 21 emitted thereby. However, it is further desired to utilize a contrast media introduced to heart 10 from an administering device 22. It is also desired to have an accurate quantitative measure of the blood flow in the tissue of left ventricle 16 which is delivered by the coronary arteries via the left ventricle blood pool, utilizing echo returns from the contrast agent which flows from left ventricle 16.

Initially, the user selects the type of anatomy, which will be scanned by the ultrasound unit. A software-controlled processor then initializes the unit's hardware modules so as to optimize the system's parameters. For example, In order achieve a quantitative blood flow measure in left ventricle tissue 16, the invention normalizes image data returned therefrom in accord with a normalization value. The normalization value is derived by examination of backscatter returns from a region of interest 24 placed in blood pool 17. Further, the invention uses echoes from the NROI to characterize the contrast agent's interaction with the incident ultrasound signals and the suitability of the contrast agent for the particular imaging modality.

Figure 2:
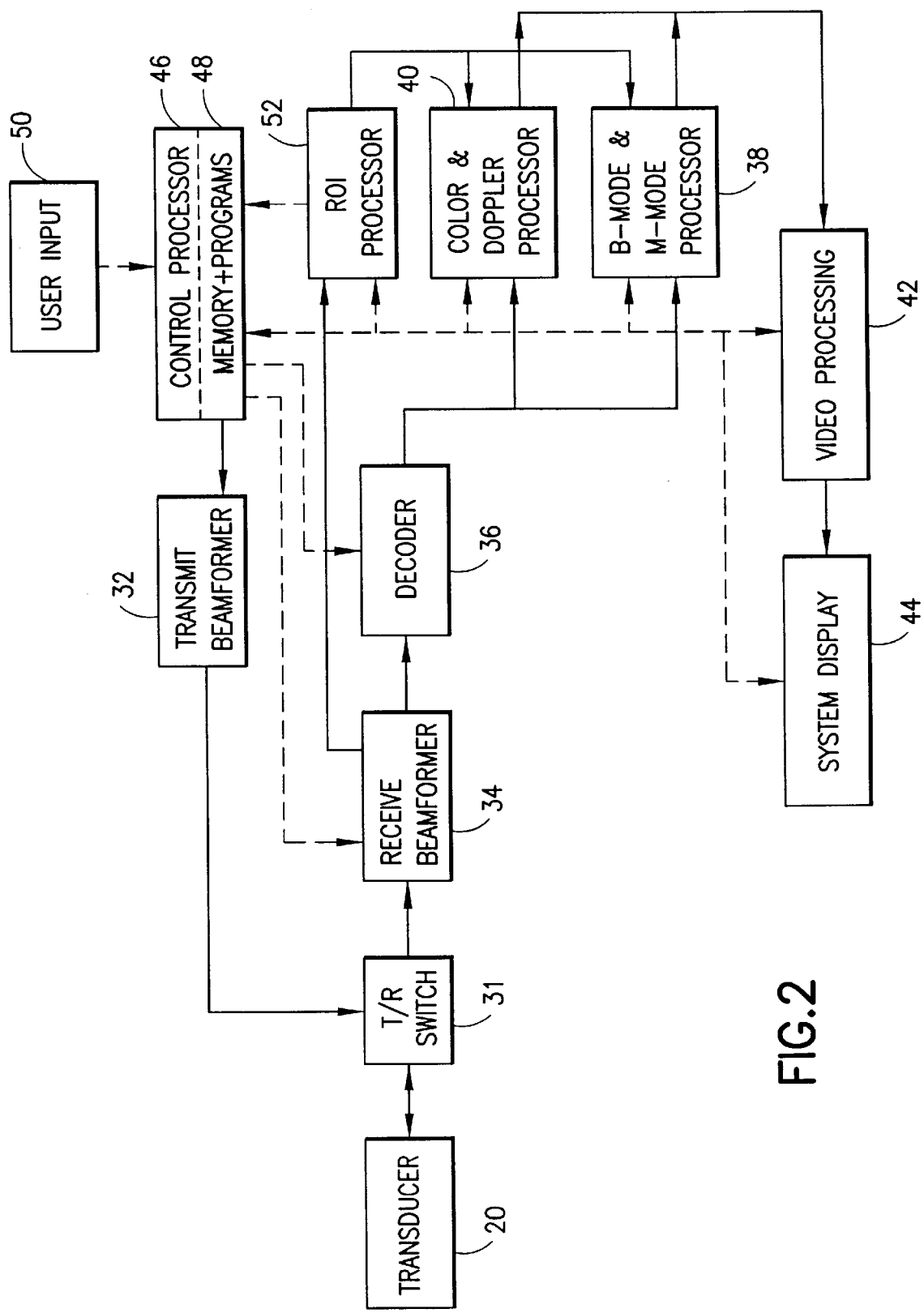
FIG. 2 is a high level block diagram of an ultrasound system incorporating the invention hereof.

Turning to FIG. 2, an ultrasound system 30 for performing the invention will be hereafter considered. Ultrasound transducer 20 is connected via a transmit/receive switch 31 to a transmit beamformer 32. Transmit beamformer 32 is set up so as to excite Transducer 20 with signals that cause the transmitted beam to have a predetermined focal location and the scanning action is set to a predetermined area with a predetermined resolution. Transmit/receive module 31 sends the signals to ultrasound transducer 20 and causes transmission of acoustic signals therefrom. When echo returns are received by ultrasound transducer 20, they are passed via transmit/receive switch 31 to a receive beamformer 34

Once the signals reach receive beamformer 34, they are focused and steered in a known manner. Detector circuitry 36 utilizes a filter technique to narrow the signals to a specific frequency spectrum of interest and quantifies both the amplitude and phase of the incoming signals. The output of detector circuitry 36 feeds several processors, which are capable of quantifying several characteristics of the detected ultrasound signal. B-Mode and M-mode processor 38 converts the amplitude of the echo signals into a range of values which are typically displayed as progressively whiter gray scale values as the amplitude of the detected signal increases.

Color Doppler processor 40 converts phase differences between consecutive line samples into tissue movement. It displays the results in a color scale indicating the velocity of the tissue at a particular location in the body. A pulse Doppler processor may also be included (not shown, that is similar to color Doppler processor 40, except the display of the information is different. Information from the pulse Doppler processor is displayed as a scrolling graph that indicates both the velocity and the amplitude of the return signal at a given location in the body or plurality of locations.

A video processor 42 receives the signals from processors 38, 40, etc. and converts them to a display format which can be visualized on a raster scan monitor 44. Overall control of the ultrasound system is carried out by a control processor 46, in conjunction with software procedures stored in memory 48 and in response to user inputs from user interface 50.

An additional processor, i.e., ROI processor 52, is shown, for the sake of simplicity, as a separate box, however, its functionality can be implemented within the detector circuitry 36. ROI processor 52 receives the pre-detected data from receive beamformer 34 and under software control, performs its own filtering and detection of the signals' amplitude and phase. ROI processor 52 receives all the information that detector 36 receives, but it processes only data which is located within a software defined NROI.

The software can define the region of interest in one of two ways. Either the user defines it using a pointing device and selecting the region on video display 44, or the software can provide a default region of interest. Data received from within the NROI is thus detected and sent to Doppler processor 40 and B-mode processor 38. The results are stored in memory 48. Control processor 46 then reads the memory locations and processes the velocity and amplitude data within the NROI.

Control processor 46 has the ability to control transmit and receive beamformers 32 and 34 within the NROI so as to interrogate the NROI, independent of the normal ultrasound scan region. The NROI data, which is stored in memory, is not limited to Doppler and B-mode information. Harmonic data, power Doppler, or any other detected data may be processed by ROI processor 52 and stored in memory 48.

The invention, at one level, provides an ability to process ultrasound echo data from an NROI by changing both transmit and receive parameters and storing the results in memory 48, independent of the standard ultrasound scan. This data provides control processor 46 with information that can be utilized to adjust the system parameters. In affect the NROI is treated as a separate ultrasound scan within the overall scan, providing control processor with a quick look at the scanning subject before it commits to a full scan of the area and provides a significant advantage in automatic system optimization and calibration.

For example, if the user instructs the ultrasound unit that it will be imaging a particular organ and then traces the organ to create an NROI, it is possible for the system to automatically adjust system parameters for the visualization of that organ. As a further example, if the user instructs the ultrasound unit that it will be performing a contrast exam and then traces an NROI at the location of the contrast agent it is possible for the system to optimize the system parameters for the detection of that particular contrast agent and also to normalize the entire scan to that particular NROI. This provides a means of quantifying the amount of agent within the body relative to the NROI.

Figure 2A:
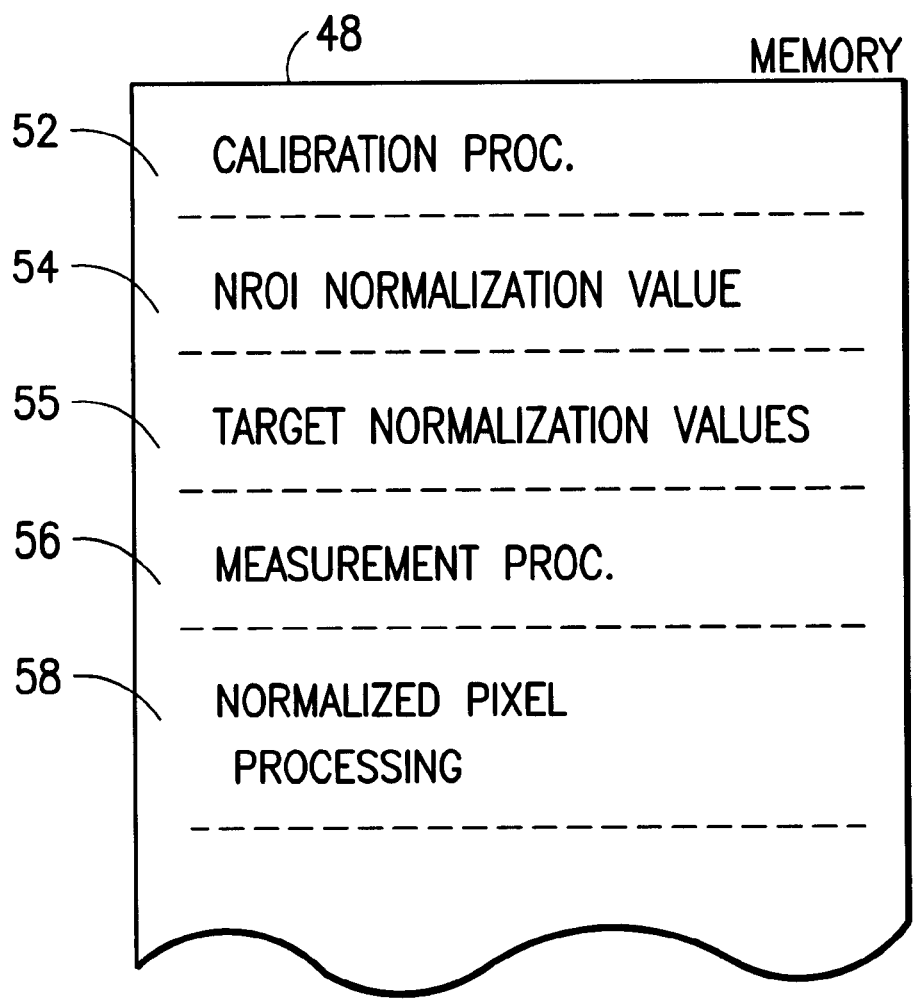
FIG. 2a is a schematic view of control programs used to the ultrasound system of FIG. 2.

To carry out the normalization action, memory 48 contains the certain procedures required to operate control processor 46 to perform the invention. Within memory 48 (as shown in FIG. 2a) is stored a calibration procedure 52 which enables acquisition and storage of a normalization value 54 from an NROI. Memory 48 further stores one or more target normalization values 55 for different modes of system operation in conjunction with a contrast media; and a measurement procedure 56 which, in turn, includes a normalized pixel processing procedure 58.

Figure 3:
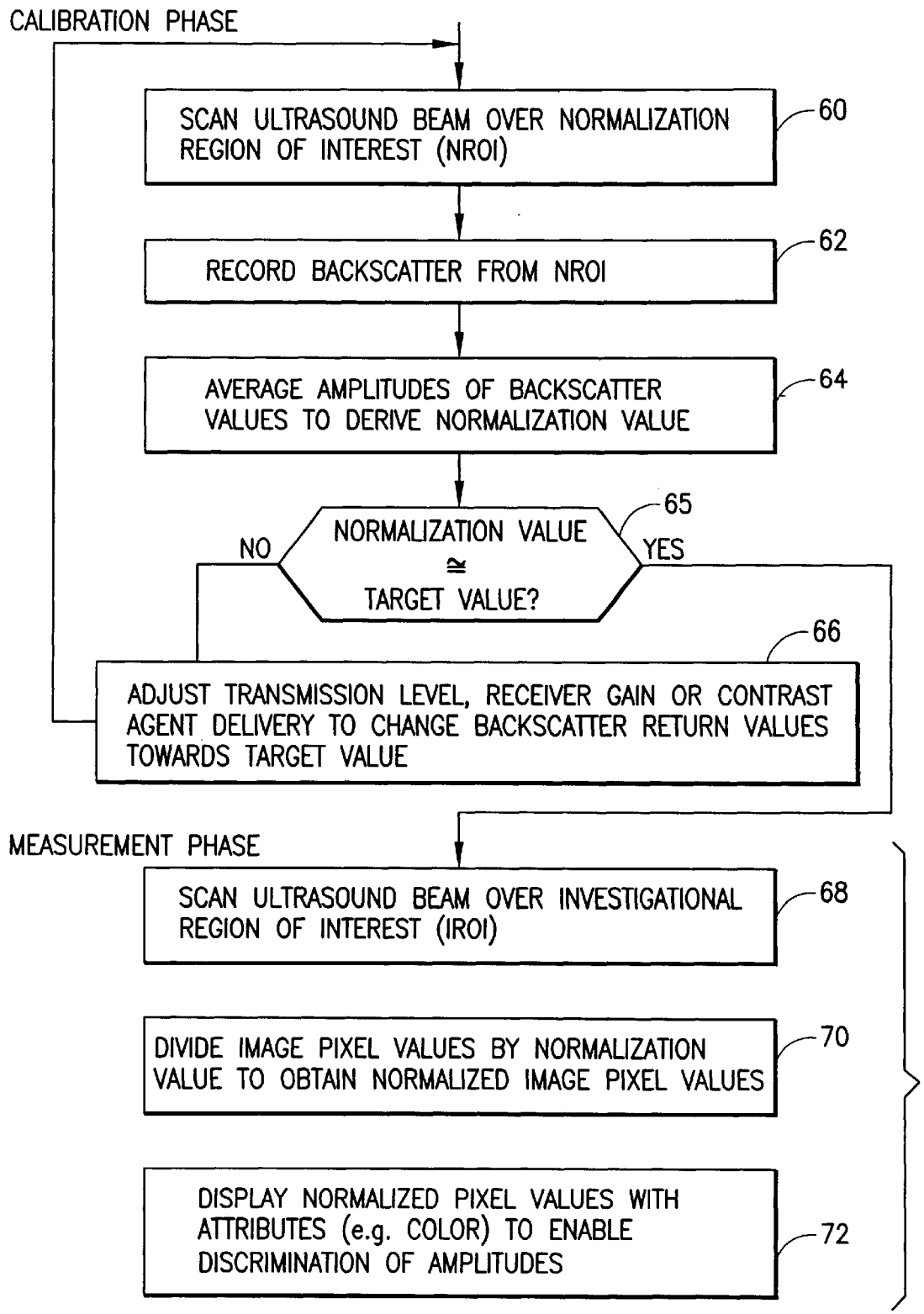
FIG. 3 is a logical flow diagram illustrating the method of the invention.

Turning to FIG. 3, the method performed under control of the aforementioned procedures will be described. As indicated above, an objective of the invention is to enable display of an investigational region of interest (i.e., IROI) with display attributes that provide the user with an accurate quantitative view of blood flow therein. Accordingly, the invention employs echo signals from the NROI to derive a normalization value which is then used to normalize the echo signals from the IROI. The normalization action removes all variables from the IROI image data, except differences in signal levels resulting from changes in quantity of contrast media passing through the IROI.

At this point, it is well to re-emphasize that the showing of FIG. 1 and the particular anatomical regions being investigated hereafter are merely for exemplary purposes. It is preferred, but not absolutely necessary, that the NROI be the source of blood for the IROI and that the normalization value be obtained from NROI echoes.

The method is divided into two phases, a calibration phase and a measurement phase. Initially, during the calibration phase (under control of calibration phase procedure 52), ultrasound beam 21 from ultrasound transducer 20 is caused to scan region of interest 24 as the NROI (step 60). The NROI is created by the user placing a geometric shape around left ventricle 16 so as to enable the ROI processor 52 to process the signals that are derived therefrom. As is known, left ventricle 16 (comprising the NROI in this example) serves as the source of blood flow for left ventricle tissue 16.

Once the NROI has been created and echo signals received therefrom, those signals are recorded (step 62). Control processor 38 then invokes calibration phase procedure 42 to control ROI processor 52 to calculate normalization value 54 from the echo signals received from the NROI. It is preferred that the amplitudes of the received echo signals be averaged over the NROI to achieve an average amplitude return value, which return value constitutes normalization value 54 to be used hereafter (step 64). It is to be understood, however, that any other calculation which properly characterizes the amplitudes of the backscatter echoes from the NROI can be utilized to obtain normalization value 54.

Thereafter (decision step 65), if calculated normalization value 54 is different from a stored target normalization value 55 in memory 48, the user is instructed to adjust a system parameter (e.g., transmit level, receiver gain, or amount/rate of contrast agent delivery) (step 66). After such adjustment, steps 60–66 are rerun in attempt to bring the normalization value 54 closer to target normalization value 55. This operation enables a minimum level of transmission power, for example, to be utilized to achieve the desired mode of operation with the contrast agent.

More precisely, if it is desired to operate in a mode where the contrast agent is not partially or completely destroyed, i.e., a linear mode, a low target normalization value 55 is utilized and repetition of steps 60–66 enables normalization value 54 to be brought towards the low target normalization value 55, through the use of system adjustments, followed by recalculation of normalization value 54. If by contrast, it is desired to operate the system in a mode wherein the contrast agent is destroyed, a higher target normalization value 55 is utilized, against which normalization value 54 is adjusted.

Once a desired normalization value 54 has been achieved, the procedure moves to measurement phase procedure 56 and ultrasound beam 21 is again scanned, but this time over IROI, e.g., pulmonary artery 18 (step 68). Thereafter, acquired pixel amplitude values are divided by previously obtained normalization value 54 to obtain normalized pixel values (step 70). Then, the normalized pixel values are processed and receive assigned attributes (e.g., colors) to enable the user to discriminate the various magnitudes of the normalized pixel values as they are displayed on display monitor 44.

As can now be understood, the use of a normalization value achieved by processing echo returns from the NROI (which serves as the blood source for the IROI), enables the elimination of variable factors that are common to both the NROI and the IROI and leaves only the contrast agent backscatter return ratio differences as the determining factors to be used for IROI pixel generation. Further, the invention enables the control of the contrast stability mode using a feedback technique that takes into account the concentration of contrast agent in the blood when performing any type of qualitative ultrasound measurement.

Processing the return from the NROI for either velocity or amplitude signatures not only provides a normalization factor, but also provides a means for measuring the contrast stability mode. The destructive contrast stability mode can easily be detected by measuring velocity information. When bubble destruction occurs, there is a high level broadband velocity signature, otherwise the Doppler signal is physiological. In addition, there are high levels of harmonic energy that are sensed. Both linear and non-linear contrast stability modes can be detected by measuring the amount of harmonic energy present in the absence of a bi-level broadband velocity signature.

Once the contrast stability mode is measured, adjustments can be made to the transmit and/or receive gain to change or maintain the desired contrast stability mode and normalization value. Further, the contrast stability mode, once determined, can provide an output which can control an infusion pump which perfuses contrast media into the patient.

Again, as stated above, by selecting the NROI in a blood pool which feeds the organ to be examined, normalization is enabled which eliminates, for example, the concentration of bubbles from the results. Further, if a destructive contrast stability mode is desired, then the system will operate at the minimum power required to destroy the bubbles. If a non-linear contrast stability mode is selected, then the harmonic response of the bubbles can be measured, while minimizing bubble destruction. This allows the user to operate at higher frame rates, potentially minimizing or eliminating the need for triggering. Linear contrast stability modes may be operated at lower power settings and ensure that the harmonic energy content is minimized.

Several of the characteristics which can be measured in vivo with this invention are:

1. Contrast agent ultrasound destruction levels and frequencies.
2. Contrast agent non-linear response to ultrasound energy.
3. Contrast agent concentration levels.
4. Contrast agent changes in concentration levels.

As indicated above, the invention can be used to quantify the amount of blood flow to or from a particular organ. In this case, the region of interest is utilized to determine the concentration of the contrast agent and to provide a normalization factor which allows the ultrasound unit to quantify the amount of agent in any other part of the image relative to the region of interest.

Another use is to utilize the region of interest to determine the contrast injection rate in vivo and to provide control to an external infusion pump to optimize the injection for a particular application.

Yet another use of the invention is to control the response of the contrast agent by adjusting the transmitted ultrasound amplitude, frequency and phase automatically for a particular modality. In much the same way the invention can be used to optimize the receive processing for the particular agent used.

In effect, any characteristic of the ultrasound contrast agent which can be measured with ultrasound can be utilized, with the invention providing feedback to the ultrasound unit which allows the unit to automatically optimize the system transmission, optimize the detection of the agent, quantify the results, control the response of the agent, determine if the agent is capable of performing the requested diagnostic modality and control an external device that provides the agent.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A method for controlling an ultrasound unit to characterize echo signals from a region of interest (ROI) and to adjust unit parameters in accord therewith, said method comprising the steps of:

a) defining a region of interest within an ultrasound image;
   b) processing received echo values from the region of interest to determine characteristics of the received echo values;
   c) adjusting at least one system parameter of said ultrasound unit to cause said received echo values from said ROI to exhibit a desired characteristic; and
   d) employing said system parameter derived in step c) to control said ultrasound unit in producing a subsequent ultrasound image that includes said ROI as a portion thereof.

2. The method as recited in claim 1, wherein said ROI includes an infused contrast agent and said at least one system parameter controls acoustic power of a transmitted beam from said ultrasound unit that insonicates said ROI.

3. The method as recited in claim 1, wherein step c) adjusts either a transmit or a receive parameter to achieve desired characteristic.

4. A system for controlling an ultrasound unit to characterize echo signals from a region of interest (ROI) and to adjust unit parameters in accord therewith, said system comprising:

a) user input means for defining a region of interest within an ultrasound image;
   b) ROI processing means dedicated to processing received echo values from the region of interest to determine characteristics of the received echo values;
   c) control processor means for adjusting at least one system parameter of said ultrasound unit to cause said received echo values from said ROI to exhibit a desired characteristic; and
   d) transmit/receive means for employing said system parameter derived by said control processor means to control said ultrasound unit to produce a subsequent ultrasound image that includes said ROI as a portion thereof.

5. The system as recited in claim 4, wherein said ROI includes an infused contrast agent and said at least one system parameter controls acoustic power of a transmitted beam from said ultrasound unit that insonicates said ROI.

6. The method as recited in claim 4, wherein said control processor means adjusts either a transmit or a receive parameter to achieve the desired characteristic.

7. A method for enabling a user to obtain from an ultrasound system a quantitative measure of blood perfusion of an investigational region of interest (IROI), comprising the steps of:

a) providing first image backscatter values from a normalization region of interest (NROI);

b) determining a normalization value which characterizes said first image echo values from said NROI;

c) providing second image backscatter values from said IROI;

d) calculating normalized values of said second image backscatter values from said IROI through use of said normalization value; and e) displaying an ultrasound image of said IROI, said image derived from said normalized values of said second image backscatter values from said IROI.

8. The method as recited in claim 7, wherein said NROI provides a source of blood for said IROI.

9. The method as recited in claim 7, wherein step b) calculates an average value of said first image backscatter values from said NROI as said normalization value.

10. The method as recited in claim 7, comprising the further step of:

b1) adjusting at least one system parameter of said ultrasound system and repeating steps a) and b) to attempt to modify said normalization value to a predetermined target value.

11. The method as recited in claim 10, wherein said system parameter is transmit power.

12. The method as recited in claim 10, wherein said system parameter is receiver gain.

13. The method as recited in claim 7, comprising the further step of:

b1) adjusting an administered amount or rate of application of a contrast agent to said NROI and repeating steps a) and b) to attempt to modify said normalization value to a predetermined target value.

14. The method as recited in claim 9, wherein said predetermined target value comprises one of plural values, said plural values associated with stability modes of use of a contrast agent, said stability modes including a mode wherein said contrast agent is not destroyed and a mode where at least a portion of said contrast agent is destroyed.

15. An ultrasound system which enables a user to obtain a quantitative measure of blood perfusion of an investigational region of interest (IROI), comprising:

a) receiver means for (i) providing first image backscatter values from a normalization region of interest (NROI), and (ii) subsequently, providing second image backscatter values from said IROI;

b) processor means (i) responsive to said first backscatter values for determining a normalization value which characterizes said image backscatter values from said NROI and (ii) responsive to said second backscatter values for calculating normalized values of said second image backscatter values from said IROI, through use of said normalization value; and c) monitor means for displaying an ultrasound image of said IROI, said image derived from said normalized values of said image backscatter values from said IROI.

16. The ultrasound system as recited in claim 15, wherein said NROI provides a source of blood for said IROI.

17. The ultrasound system as recited in claim 15, wherein said processor means calculates an average value of said first image backscatter values from said NROI as said normalization value.

18. The ultrasound system as recited in claim 15, wherein said processor means, after adjustment of at least one system parameter of said ultrasound system, causes said receiver means to repeat operation i) and subsequently recalculates said normalized value of said second image backscatter values from said NROI to attempt to modify said normalization value to a predetermined target value.

19. The ultrasound system as recited in claim 18, wherein said system parameter is transmit power.

20. The ultrasound system as recited in claim 18, wherein said system parameter is receiver gain.

21. The ultrasound system as recited in claim 15, wherein after adjustment of an administered amount or rate of application of a contrast agent to said NROI, said processor means causes said receiver means to repeat operation i) and subsequently recalculates said normalized value of said second image backscatter values from said NROI to attempt to modify said normalization value to a predetermined target value.

22. The ultrasound system as recited in claim 18, wherein said predetermined target value can comprise one of plural values, said plural values associated with stability modes of use of a contrast agent, said stability modes including a mode wherein said contrast agent is not destroyed and a mode where at least a portion of said contrast agent is destroyed.

* * * * *